(12) United States Patent
Whitney

(10) Patent No.: US 9,339,570 B2
(45) Date of Patent: May 17, 2016

(54) ULTRAVIOLET GERMICIDAL IRRADIATION CABINET AND COMPONENTS AND FEATURES THEREFOR

(71) Applicant: Edlund Company, LLC, Burlington, VT (US)

(72) Inventor: Ryan S. Whitney, Essex Junction, VT (US)

(73) Assignee: Edlund Company, LLC, Burlington, VT (US)

( * ) Notice: Subject to any disclaimer, the term of this patent is extended or adjusted under 35 U.S.C. 154(b) by 0 days.

(21) Appl. No.: 14/614,000

(22) Filed: Feb. 4, 2015

(65) Prior Publication Data

US 2015/0217010 A1 Aug. 6, 2015

Related U.S. Application Data

(60) Provisional application No. 61/936,071, filed on Feb. 5, 2014.

(51) Int. Cl.
*A61L 2/10* (2006.01)
*A61L 9/20* (2006.01)

(52) U.S. Cl.
CPC ............... *A61L 2/10* (2013.01); *Y10T 29/49826* (2015.01)

(58) Field of Classification Search
CPC ........... A61L 2/10; A61L 2/0047; A61L 2/08; A61L 9/20; C02F 1/325
USPC ........ 250/455.11, 492.1, 504 R, 372, 454.11, 250/461.1, 365
See application file for complete search history.

(56) References Cited

U.S. PATENT DOCUMENTS

| | | | | |
|---|---|---|---|---|
| 5,016,292 A * | 5/1991 | Rademacher | ........... | A61F 9/022 128/858 |
| 7,397,041 B1 * | 7/2008 | Leonard | .................... | A61L 2/10 250/453.11 |
| 7,560,706 B1 * | 7/2009 | Castelluccio | ............ | A61L 2/10 250/365 |
| 8,633,454 B2 * | 1/2014 | Durkin | ....................... | A61L 2/10 215/11.6 |
| 8,791,441 B1 * | 7/2014 | Lichtblau | .................. | A61L 2/10 250/455.11 |
| 8,872,130 B1 * | 10/2014 | Matthews | ............... | C02F 1/325 210/764 |
| 9,095,633 B1 * | 8/2015 | Dayton | ..................... | A61L 2/10 |
| 2006/0017025 A1 * | 1/2006 | Jensen | ................. | H05B 3/0033 250/504 R |

(Continued)

OTHER PUBLICATIONS

Sofinor Cabinet with Removable Steel Basket; http://www.sofinor.com/en/catalog-330-179-199-3-3-14-110-0.html. 2011.

(Continued)

*Primary Examiner* — David A Vanore
(74) *Attorney, Agent, or Firm* — Downs Rachlin Martin PLLC

(57) ABSTRACT

A sanitization cabinet for sanitizing items such as kitchen utensils using ultraviolet light type C (UVL-C). In some embodiments, the sanitization cabinet includes an enclosure having interior surfaces having mirror-type surfaces to increase the sanitizing efficiency relative to conventional UVL-C cabinets having like-power UVL-C light sources. Some embodiments include an article support having an article support region that contacts an article to be sanitized and is made of a material transparent to UVL-C. Transparent portions of an article support of the present disclosure may be additionally configured to direct UVL-C to contact regions and/or shadowed regions of the article. Other features, such as article stabilizing features, are provided to article supports of some embodiments. Methods of making an article support for a UVL-C based sanitization cabinet are also disclosed.

19 Claims, 5 Drawing Sheets

(56) References Cited

U.S. PATENT DOCUMENTS

| | | | | |
|---|---|---|---|---|
| 2007/0045561 A1* | 3/2007 | Cooper | .................. | A61L 2/10 250/453.11 |
| 2007/0051901 A1* | 3/2007 | Hopaluk | .................. | C02F 1/325 250/436 |
| 2007/0192986 A1* | 8/2007 | Garcia | .................. | A47L 9/00 15/339 |
| 2007/0192987 A1* | 8/2007 | Garcia | .................. | A47L 9/00 15/339 |
| 2007/0194255 A1* | 8/2007 | Garcia | .................. | A61L 2/10 250/504 R |
| 2008/0061252 A1* | 3/2008 | Garcia | .................. | A61L 2/10 250/504 H |
| 2009/0218512 A1* | 9/2009 | Ranta | .................. | A61L 2/10 250/455.11 |
| 2009/0294688 A1* | 12/2009 | Evans | .................. | A23L 3/28 250/436 |
| 2010/0193709 A1* | 8/2010 | Dalton | .................. | A61L 2/10 250/504 R |
| 2011/0162155 A1* | 7/2011 | Wai | .................. | A46B 15/0002 15/4 |
| 2011/0215261 A1* | 9/2011 | Lyslo | .................. | A61L 2/10 250/492.1 |
| 2012/0006995 A1* | 1/2012 | Greuel | .................. | C02F 1/325 250/373 |
| 2012/0126134 A1* | 5/2012 | Deal | .................. | A61L 2/10 250/372 |
| 2012/0223216 A1* | 9/2012 | Flaherty | .................. | A61L 2/10 250/214.1 |
| 2012/0261593 A1* | 10/2012 | Noori | .................. | A61L 2/10 250/492.1 |
| 2012/0305787 A1* | 12/2012 | Henson | .................. | A61L 2/10 250/372 |
| 2012/0305804 A1* | 12/2012 | Goldman | .................. | E05B 1/0069 250/492.1 |
| 2013/0126760 A1* | 5/2013 | Klein | .................. | A61L 2/10 250/492.1 |
| 2013/0214174 A1* | 8/2013 | Domenig | .................. | G02B 5/0278 250/455.11 |
| 2014/0061509 A1* | 3/2014 | Shur | .................. | A23L 3/003 250/492.1 |
| 2014/0084179 A1* | 3/2014 | Ben-Hur | .................. | A61M 1/3681 250/429 |
| 2014/0175280 A1* | 6/2014 | Tantillo | .................. | A63H 33/006 250/338.1 |
| 2014/0208541 A1* | 7/2014 | Cowburn | .................. | E05B 1/0069 16/110.1 |
| 2014/0264070 A1* | 9/2014 | Bettles | .................. | A61L 2/10 250/430 |
| 2014/0264074 A1* | 9/2014 | Victor | .................. | A61L 2/10 250/455.11 |
| 2015/0069270 A1* | 3/2015 | Shur | .................. | F25D 17/042 250/492.1 |
| 2015/0115170 A1* | 4/2015 | Shostak | .................. | A61L 2/10 250/429 |
| 2015/0196674 A1* | 7/2015 | Newham | .................. | A61L 2/10 250/455.11 |
| 2015/0209457 A1* | 7/2015 | Bonutti | .................. | A61L 2/10 250/435 |
| 2015/0217011 A1* | 8/2015 | Bettles | .................. | A61L 2/24 250/435 |

OTHER PUBLICATIONS

Sofinor Cabinet with Magnetic Bar; http://www.sofinor.com/en/catalog-330-179-199-3-3-13-109-0.html; 2011.

* cited by examiner

ULTRAVIOLET GERMICIDAL IRRADIATION CABINET AND COMPONENTS AND FEATURES THEREFOR

RELATED APPLICATION DATA

This application claims the benefit of priority of U.S. Provisional Patent Application Ser. No. 61/936,071, filed on Feb. 5, 2014, and titled "ULTRAVIOLET GERMICIDAL IRRADIATION CABINET AND COMPONENTS AND FEATURES THEREFOR," which is incorporated herein by reference in its entirety.

FIELD OF THE INVENTION

The present invention generally relates to the field of sanitization. In particular, the present invention is directed to an ultraviolet germicidal irradiation cabinet and components and features therefor.

BACKGROUND

Germicidal irradiation using shortwave ultraviolet light (UVL-C) has long been used for killing germs. The foodservice industry, for example, utilizes UVL-C germicidal irradiation sanitization cabinets that allow food-service providers to sanitize food preparation and handling equipment, such as kitchen and eating utensils. For example, various vendors sell UVL-C based sanitization cabinets for sanitizing knives.

SUMMARY

In one implementation, the present disclosure is directed to a sanitization cabinet. The sanitization cabinet includes an enclosure forming a sanitization space designed and configured to receive at least one article to be sanitized, the enclosure having a plurality of interior surfaces each having a surface finish for reflecting ultraviolet light type C (UVL-C) within sanitization space; a UVL-C source located so as to provide UVL-C to the sanitization space; and an article support having at least one article support region designed and configured to supportingly contact the at least one article at a corresponding contact zone, wherein the article support region is made of a UVL-C-transparent material that allows UVL-C from the UVL-C source to illuminate the contact zone.

In another implementation, the present disclosure is directed to an article support for a sanitizing cabinet that uses ultraviolet light type C (UVL-C) from at least one UVL-C source to sanitize at least one article. The article support includes at least one support region designed and configured to supportingly contact the at least one article at a corresponding contact zone, wherein the support region is made of a UVL-C-transparent material that allows UVL-C from the UVL-C source to illuminate the contact zone; wherein the article support is designed and configured to be supportingly installed within the sanitizing cabinet.

In still another implementation, the present disclosure is directed to a method of manufacturing an article support for an ultraviolet light type C (UVL-C) based sanitization cabinet. The method includes determining an article to be supported by the article support when the article support is installed in the sanitization cabinet and the article is placed in the sanitization cabinet for sanitizing with the UVL-C during a sanitization operation; locating on the article support an article support region wherein the article will be supported by the article support and will have a contact region in contact with the article support region when the article support is supporting the article within the sanitization cabinet during the sanitization operation; and manufacturing the article support to provide a UVL-C transparent material at the article support region so that UVL-C can reach the contact region of the article when the article support region is supporting the article within the sanitization cabinet during the sanitization operation.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
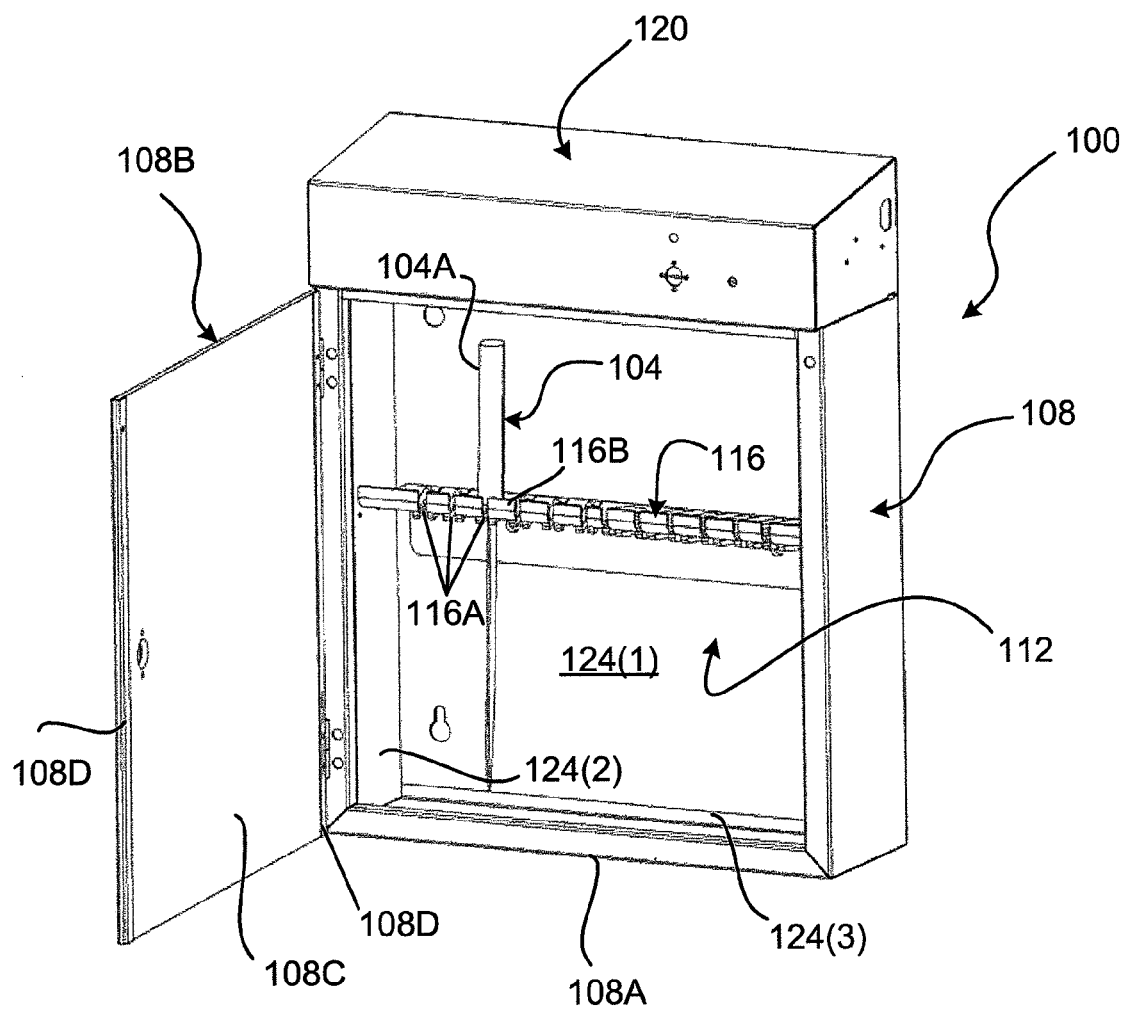
FIG. 1 is a front perspective view of a ultraviolet light type C (UVL-C) based sanitization cabinet made in accordance with the present invention, showing a kitchen knife supported by a UVL-C transparent support.

The present inventor has found that in the context of sanitizing kitchen knives in commercial kitchens, when the knives are supported in a conventional type-C ultraviolet light (UVL-C) based sanitization cabinet, such as by a conventional strip-type magnetic holder in which a knife blade is in direct contact with the magnetic strips of the holder, the UVL-C does not reach the parts of the knife blade contacting the magnetic strips. The same problem exists with other types of conventional article holders, such as wire racks and hooks, where the knives directly contact the holders. In addition, much of the UVL-C does not reach portions of the knife blade that confront but do not necessarily touch the holder because of excessive shadowing. Therefore, each knife is not 100% sanitized. In addition, the present inventor has also found that conventional UVL-C sanitization cabinets, which have interior surfaces of poor light-reflectivity, have relatively low sanitizing efficiencies in terms of the amount of time per watt of the UVL-C source it takes to complete a sanitization cycle, that is, the amount of time per watt it takes to achieve a target level of sanitization for an exposed surface of the article being sanitized. With this measure, the lower the amount of time per watt, the higher the efficiency, and vice versa.

In connection with solving at least these shortcomings of conventional UVL-C sanitization, the present inventor has developed UVL-C sanitization cabinets and components thereof that permit efficient and effective UV germicidal irradiation of 100% of the outer surface of each article placed into such a cabinet and/or high-efficiency sanitation cycles, i.e., sanitation cycles that have sanitation efficiencies substantially higher than conventional UVL-C sanitization cabinets. It is noted that the term "cabinet" and like terms as used in the present description and any appended claims is intended to have a broad meaning that includes not only self-contained structures that can be, for example, mounted to walls, mounted on casters, or freestanding, but also to similar structures that are built into larger structures, such as under-counter or over-counter cabinetry and mobile or fixed multi-functional workstations, among other things. As will be understood by those skilled in the art, features and aspects of the present invention can be used singly or together in various combinations to achieve the desired functionality and/or desired performance. For the sake of illustrating the present invention, the various aspects and features thereof are presented in the context of specific embodiments shown in the accompanying drawings and described below. While specific embodiments are used for illustrative purposes, those skilled in the art will readily appreciate that the aspect and features that underlie these embodiments can readily be implemented, alone and in various combinations, in a wide range of UVL-C sanitization cabinets, all of which are encompassed by the present invention.

Figure 2:
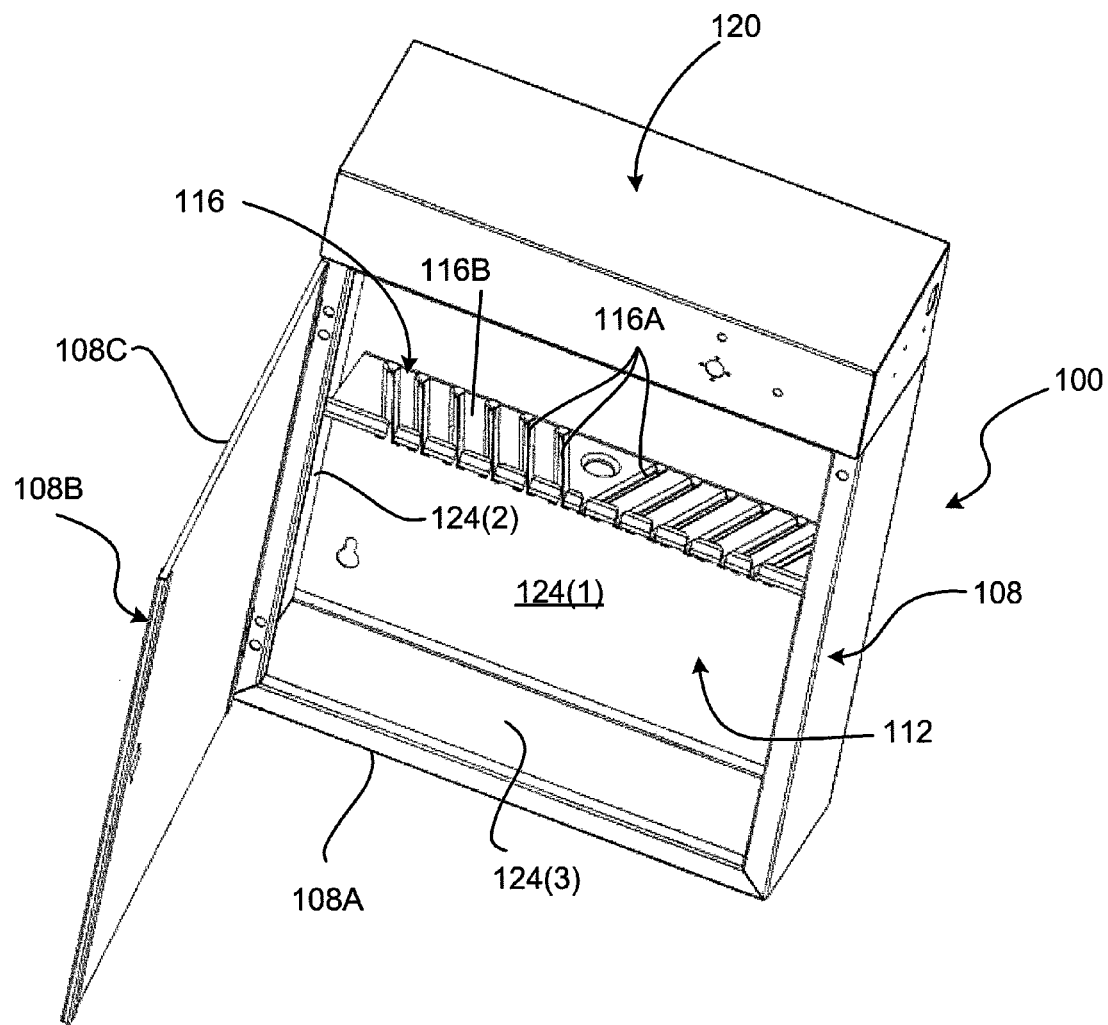
FIG. 2 is a front-tilted perspective view of the sanitization cabinet of FIG. 1.
Figure 3:
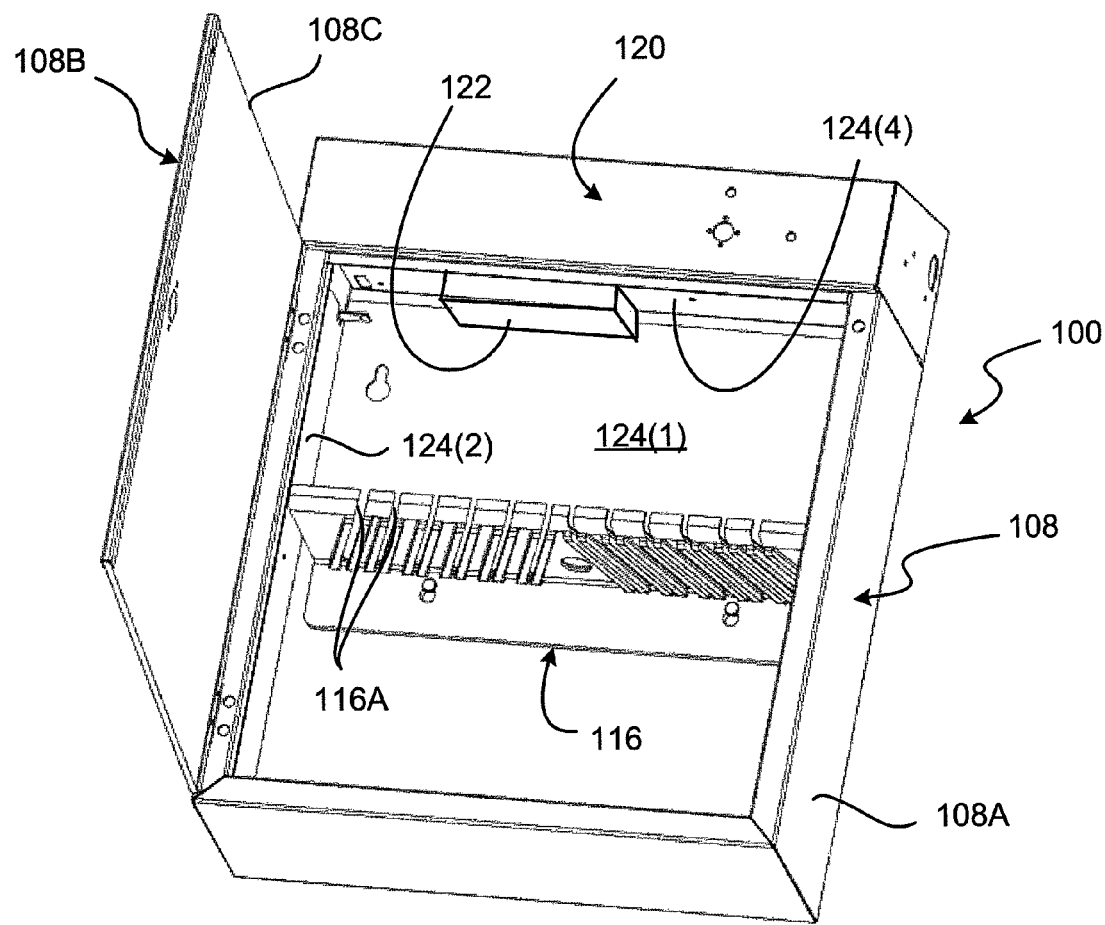
FIG. 3 is a back-tilted perspective view of the sanitization cabinet of FIG. 1.

Referring now to the drawings, FIGS. 1-3 illustrate an exemplary UVL-C sanitization cabinet 100 that includes a number of features that allow it to sanitize 100% of the surfaces of each article sanitized using the cabinet, here, a kitchen knife 104, and allow it to have a high sanitizing efficiency. In this example, sanitization cabinet 100 comprises an enclosure 108 that defines a sanitization space 112 that receives the one or more articles, such as knife 104, to be sanitized. It is noted that sanitization cabinet 100 is particularly configured for sanitizing kitchen knives by virtue of the configuration of its article support 116, which is a knife support having slots 116A each designed and configured to receives the blade of a corresponding knife, such as knife 104, so that the lower end of the knife handle, here handle 104A, rests on an upper surface 116B of the support to allow the knife to be suspended by the support. It is noted that the knife-rack type of article support 116 shown is but one of many differing designs that can be implemented for supporting one or more knives within sanitization space 112. Moreover, this knife-rack embodiment of article support 116 can readily be replaced by an article support of another type specifically designed and configured to support another type of article, such as one or more other types of kitchen or eating utensil, any one or more of a variety of medical equipment, any one or more pieces of laboratory ware and/or equipment, among many other types of articles.

Figure 6:
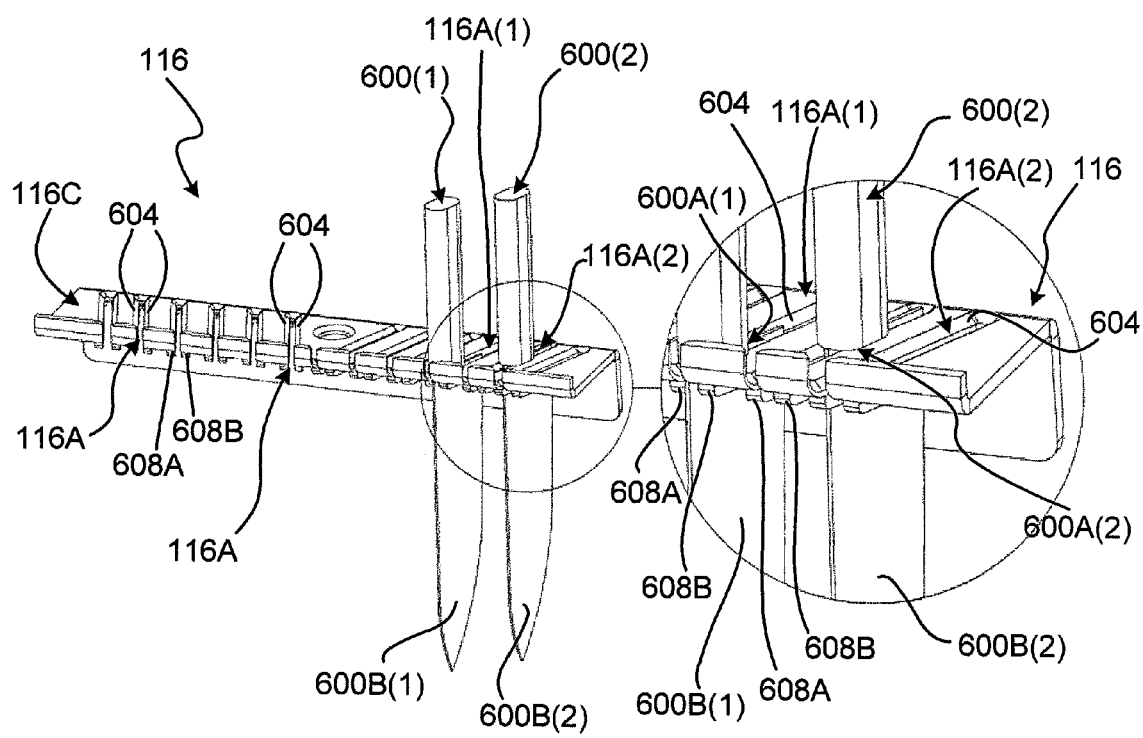
FIG. 6 is a combined isometric view/enlarged detail view of the article support of the sanitization cabinet of FIGS. 1-3.

While many other article supports can be used for article support 116, the knife-support version illustrated in FIGS. 1-3 has several unique physical features that make it particularly suitable for use with a high-effectiveness sanitization cabinet, such as sanitization cabinet 100, and these features are particularly seen in FIG. 6. Referring to FIG. 6, article support 116, referred to in this detailed description of FIG. 6 as "knife rack 116" because it is primarily designed to support knives, is shown supporting two knives 600(1) and 600(2) in corresponding respective slots 116A(1) and 116A(2). In this embodiment, knife support 116 is designed to keep knives 600(1) and 600(2) vertical and spaced from one another so that they do not touch one another. As noted above, when articles, knives for example, touch each other, shadowing occurs, and shadowing inhibits the shadowed regions from being properly sanitized. In some conventional vertical-hanging-style knife holders, the upper surfaces of the holders on which the knife handles rest are flat. However, the hilts of many knives are tapered, and when these knives are placed in such flat-topped holders, they tend to pivot due to the tapered hilts, often causing them to contact each other. In knife support 116, however, each slot 116A has opposing chamfered edges 604 (only a few labeled for convenience and to avoid clutter) that accommodatingly received tapered hilts 600A(1) and 600A(2) of corresponding respective knives 600(1) and 600(2) in a manner that reduces the likelihood that the knives will pivot and touch one another.

Also in the embodiment shown, knife holder 116 includes a pair of pivot stops 608A and 608B (only several labeled for convenience and to avoid clutter) at each slot 116A. Pivot stops 608A and 608B are located on the underside of knife holder 116 and depend therefrom along a vertical height selected such that if a particular knife, such as either of knives 600(1) and 600(2), begins to pivot laterally, one or the other of the stops will keep the pivoting from becoming so excessive that contact between two knives or between a knife and an interior wall of the sanitization cabinet occurs. As those skilled in the art will readily appreciate, the vertical height of each pivot stop 608A and 608B can be determined based upon a number of factors, such as the width of the corresponding slot 116B, the design thickness for the knife blade, and the thickness of the horizontal portions 116C of knife holder 116. Another feature of knife holder 116 is that slots 116B are relatively long. This length provides a number of useful features, including the ability to accommodate large cutting utensils, such as butcher knives and cleavers, and the ability to stagger the relative positions of the knives in adjacent slots 116B. This can be seen to some extent in FIG. 6 with knife 600(1) being located farther forward in slot 116(1) than knife 600(2) in slot 116(2). This staggering can increase the amount of light that hits the knives per unit of time to decrease the length of a sanitization cycle. In this connection, it is noted that slots 116B are skewed to allow for longer slots without increasing the depth of sanitization cabinet 100 (FIGS. 1-3) and may also increase the exposure of the knives in knife holder 116 because of the orientation of the faces of blades 600B(1) and 600B(2) relative to the reflective interior surface of the cabinet.

Referring again to FIGS. 1-3, it is further noted that while sanitization cabinet 100 is shown as having a single article support 116, other sanitization cabinets made in accordance with the present invention can contain multiple article supports. For example, some sanitization cabinets may have multiple rows and/or multiple columns of the same type of article support depending on the configurations of the particular sanitization cabinets at issue and/or on the maximum number of articles each cabinet is designed to hold. As another example, ones of such multiple rows and/or columns of article supports may be designed and configured to receive specific differing types of articles. For example, a single sanitization cabinet may include four article supports designed and configured for four differing types of articles, such as knives, forks, spoons, and tongs. Further, depending upon the configuration(s) of the article(s) at issue, each article may require two or more article supports, such as a mid-height support and a bottom support, among many other arrangements. Fundamentally, there is no constraint on the number and location(s) of the article support(s) within a sanitization cabinet of the present disclosure, nor the type of article(s) supported, other than constraints of practicality.

In the embodiment shown, sanitization cabinet 100 includes a housing 120 that may house or otherwise support one or more UVL-C sources 122 (FIG. 3), each of which can be any suitable conventional UVL-C source, including a non-phosphor-coated fluorescent lamp, among others. The particular type(s) of UVL-C source(s) 122 is/are not important as long as each emits the necessary or desired amount of UVL-C. As those skilled in the art will understand, each UVL-C source 122 need not be located as shown, but rather may be located at any suitable location that provides UVL-C to sanitization space 112 within enclosure 108. Housing 120 may also contain other components, such as power transformer(s), locking mechanism(s), timer(s), electronics for any display(s), switch(es), and/or electronics for controlling the operation of sanitization cabinet 100, among other things. Those skilled in the art will readily appreciate that while housing 120 is shown as being on the top of sanitization cabinet 100 in this example, in other embodiments in which such a housing are provided the housing may alternatively be provided on one side or the other, on the bottom, or on the front or back. In addition, a sanitization cabinet of the present invention can have more than one housing as desired to suit a particular arrangement of components.

In this embodiment, enclosure 108 includes a body portion 108A and a closure 108B movable relative to the body portion to allow a user to access sanitization space 112 for inserting and removing articles to be sanitized. Regarding materials of construction, body portion 108A may be made of any suitable material that is opaque to at least UVL-C to inhibit UVL-C from exiting sanitization space 112. In many cases, it is also desirable for body portion 108A to be easy to clean. Consequently, it is anticipated that many embodiments of a sanitization cabinet made in accordance with the present invention will have their body portions made of stainless steel or another UVL-C opaque material having superior cleanability and sanitizability. Similarly, closure 108B may be made of a suitable UVL-C opaque material, such as stainless steel (or other metal), UVL-C blocking glass, or UVL-C blocking plastic, or any combination thereof. In the embodiment shown, closure 108B is primarily made of a sheet 108C of UVL-C blocking glass and a pair of end channels 108D that facilitate mounting the sheet of glass to body portion 108A and protecting the corresponding respective edges of the glass sheet. In this example, sheet 108C is transparent to visible light to the extent that a viewer can view the contents of sanitization cabinet 100 at least while the cabinet is in a sanitizing cycle.

As noted above, a deficiency the present inventor has noted in conventional sanitization cabinets, at least sanitization cabinets for the food-service industry, is that the interior surfaces of the enclosures have poor reflectivity, which manifests itself in lower sanitization efficiency, inefficient energy usage, and longer sanitization times. Those cabinets typically have enclosures and doors made of brushed stainless steel sheet metal. As those skilled in the art will readily understand, UVL-C reflectivity of brushed stainless steel is relative low. Sanitization cabinet 100 of the present invention, however, has interior surfaces, such as interior surfaces 124(1) to 124 (4), that are relatively highly polished to provide a mirror-type finish that reflects substantially more UVL-C than conventional brushed stainless steel. In the context of constructing enclosure of stainless steel, examples of surface finishes for stainless steel that provide mirror finishes include bright annealed (BA), 2BA (i.e., BA plus rolled with polished rolls), No. 7, No. 8, and temper rolled (TR) finishes as defined by the Specialty Steel Industry of North America (SSINA) trade association, Washington, D.C. (www.ssina.com). These finishes are designated in the appended claims, respectively, as an "SSINA BA finish", an "SSINA 2BA finish", an "SSINA No. 7 finish", an "SSINA No. 8 finish", and an "SSINA TR finish". It is noted that materials other than stainless steel can be used to provide, in comparable manner relative to the stainless steel finished noted above, mirror-type reflectivity in the appropriate wavelength(s), including actual mirrors made using reflective coatings on appropriate substrates. The term "mirror-type reflectivity" as used herein and in the appended claims means a reflectivity that allows a human observer to see a reflected image of an object, such as a card from a deck of playing cards, and to discern details of the object, such as graphic depicting a king of a face card, in the object's reflection from a surface having such mirror-type reflectivity. As those skilled in the art will appreciate, with higher UVL-C reflectivities of the interior surfaces of a sanitizing cabinet, such as interior surfaces 124(1) to 124(4) of sanitizing cabinet 100, far more UVL-C light can reach the article(s) within sanitizing space, here, sanitizing space 112, and more UVL-C light translates into shorter sanitizing cycles, and hence, power usage, for a given power of UVL-C source(s) 122.

Importantly, article support 116 comprises, at least at the critical location(s) where the article(s) contact the article support and/or where the article support would create a shadow on each article if the support were not transparent to UVL-C, one or more materials that are substantially or completely transparent to UVL-C. As also noted above, the present inventor has found that conventional sanitization cabinets are plagued by the use of UVL-C opaque materials for the article holders within the sanitization cabinets. These opaque materials cause shadowing of the UVL-C that results in incomplete sanitization because the shadowed regions are not irradiated with the germicidal UVL-C. This leaves less than 100% of the articles sanitized. In addition, for kitchen knives in particular, conventional sanitization cabinets often have strip-type magnetic holders that engage the blades of the knives. Of course, the blades are the parts of knives that most frequently touch the foods they are used to cut, and this results in a high likelihood that any germs remaining at the shadowed regions of the blades contaminate the food.

In contrast and in the present invention, within at least the shadowing and contacted regions of article support 116, the article support is made of one or more materials that are transparent to UVL-C to the extent that UVL-C reaches the contacting and shadowed regions of the corresponding respective article being supported by the article support in amounts suitable for sanitizing the shadowed and contacting regions of the supported article in substantially the same amount of time and to the substantially same level of sanitization as non-shadowed and non-contacted regions of that supported article. It is noted that in the immediately preceding explanation, the terms "shadowing" and "shadowed" relate to the shadowing and shadowed effects that would be present if article support 116 were not made of one or more effectively UVL-C transparent materials and/or the articles contacting one another or a wall of cabinet 100. This is so because, since article support 116 has UVL-C transparency, there effectively is no shadowing since the UVL-C passes through and/or otherwise reaches the contacting and shadowed regions of the supported article.

Depending on the configuration of article support 116 and the locations of the contacting and shadowed regions of each article being supported by the article support relative to the location(s) of UVL-C source(s) 122, in the shadowing and contacted regions of the article support the article support can be shaped and otherwise configured to act as a UVL-C guide that guides UVL-C to the contacting and/or shadowed regions of the supported article. Such shaping and configuring can include, but not be limited to, creating facets and other structures that allow the article support to collect UVL-C and guide the collected UVL-C internally within article support 116 to the contacting and/or shadowed regions of each supported article. Examples of materials having effective UVL-C transparency include but are not limited to polycarbonate (e.g., LEXAN® plastic) and polyethylene terephthalate glycol (PTEG), among others. In some embodiments, such as the embodiment shown, each article support, here article support 116, may be made entirely of one or more UVL-C transparent materials. As mentioned above, in other embodiments, only the affected regions, i.e., the shadowing and contacted regions, of each article support is made of one or more UVL-C transparent materials, with parts outside those regions being made of one or more materials that are not transparent to UVL-C.

Figure 4:
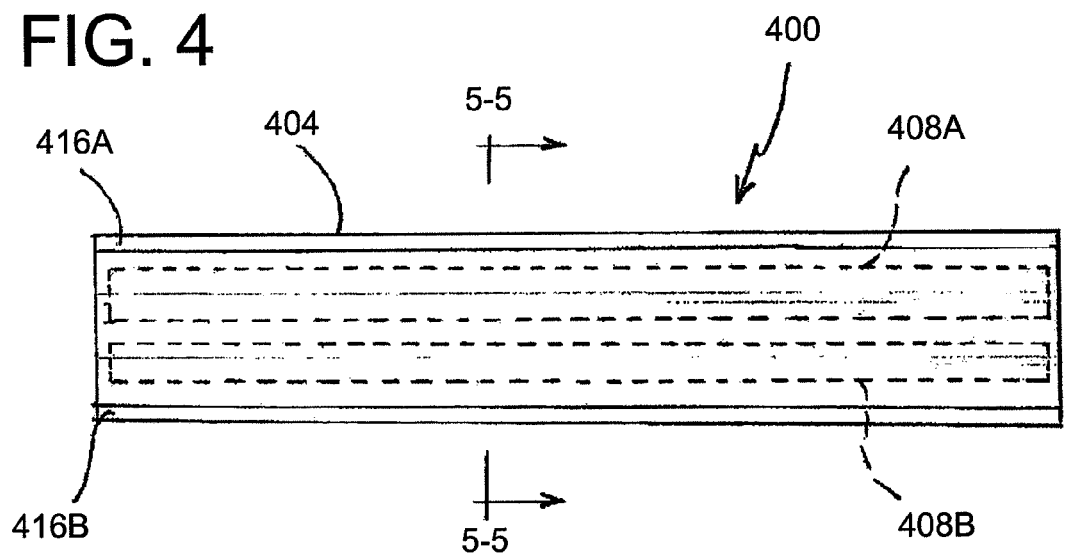
FIG. 4 is a front view of article support that can be used in a UVL-C based sanitization cabinet, wherein the article support includes magnets for supporting an article comprising a ferromagnetic material.
Figure 5:
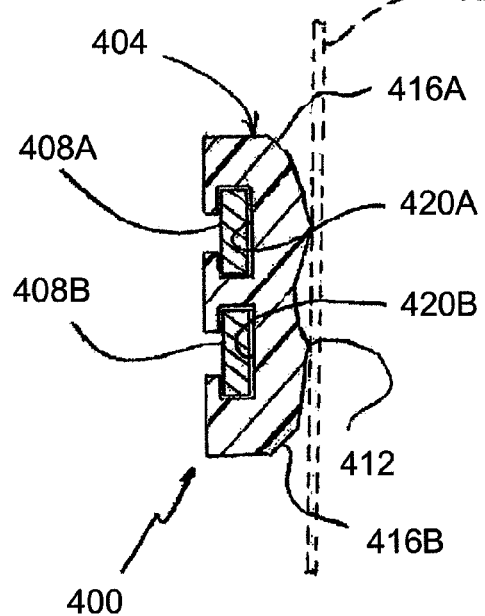
FIG. 5 is an enlarged cross-sectional view as taken along line 5-5 of FIG. 4.

Whereas FIGS. 1-3 illustrate a rack-type article support 116, FIGS. 4 and 5 illustrate a magnetic-strip-type article support 400. Referring to FIGS. 4 and 5, article support 400 is a knife-type support configured in a way that it guides UVL-C within a UVL-C sanitization cabinet, such as sanitization cabinet 100 of FIGS. 1-3, to regions of the knives it supports that would otherwise not be exposed to the light due to contact with the knife support, shadowing, or otherwise not being in a path of the UVL-C.

In the example shown in FIGS. 4 and 5, article support 400 includes two primary components, a knife-engaging component, here a strip 404, and a magnetic component, here magnets 408A, 408B. Strip 404 is made of a material that is effectively UVL-C transparent, and magnets 408A, 408B are spaced from the knife-engaging surface 412 of the strip by portions of the strip itself. Because of the UVL-C transparency and the spacing of knife-engaging surface 412 from magnets 408A, 408B, UVL-C can enter into strip 404 at various locations, reflect internally within the strip, and exit the strip at the location of a knife blade so as to expose that blade where it confronts the strip. In the present embodiment, magnets 408A, 408B are rare-earth magnets that are highly polished such that they assist in reflecting UVL-C toward the portion of the knife blade confronting strip 404. Strip 404 in this example is made out of polycarbonate plastic, LEXAN® plastic to be specific. This type of plastic is National Sanitation Foundation approved. As noted above, strip 404 could alternatively be made of PETG, among other UVL-C-transparent materials.

As seen in FIG. 5, knife-engaging surface 412 is contoured to provide essentially two narrow strips of contact with a knife blade 500. The top and bottom outer edges 416A and 416B are chamfered to increase the light gathering ability of strip 404. As is also seen in this example, magnets 408A, 408B are located in corresponding respective channels 120A and 120B. It is noted that holder 400 can also be used outside of a UV-light cabinet, as well. For example, LEXAN® plastic and PETG, among others, are nonporous, unlike the magnets of some conventional knife holders that contact the knives. As is well known, porous materials can provide breeding grounds for bacteria, and having knives or other kitchen utensils in contact with such materials can contaminate the utensils. In contrast, when article support 400 is made using a nonporous plastic or other material, the magnetically supported articles only contact the non-porous, less contamination prone, strip 404, which reduces the likelihood of contaminating the supported articles.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A sanitization cabinet, comprising:
   an enclosure forming a sanitization space designed and configured to receive at least one article to be sanitized, said enclosure having a plurality of interior surfaces each having a surface finish for reflecting ultraviolet light type C (UVL-C) within sanitization space, wherein said surface finish has a mirror-type reflectivity, said interior surfaces comprise surfaces of stainless steel, and said surface finish is selected from a group consisting of an SSINA BA finish, an SSINA 2BA finish, an SSINA No. 7 finish, an SSINA No. 8 finish, and an SSINA TR finish;
   a UVL-C source located so as to provide UVL-C to said sanitization space; and
   an article support having at least one article support region designed and configured to supportingly contact the at least one article at a corresponding contact zone, wherein said article support region is made of a UVL-C-transparent material that allows UVL-C from said UVL-C source to illuminate the contact zone.

2. A sanitization cabinet according to claim 1, wherein said surface finish is selected from a group consisting of said SSINA No. 7 finish and said SSINA No. 8 finish.

3. A sanitization cabinet according to claim 1, wherein said article support is a kitchen utensil support designed and configured to suspend one or more kitchen utensils within said sanitization space.

4. A sanitization cabinet according to claim 1, wherein said UVL-C transparent material comprises polyethylene terephthalate glycol.

5. A sanitization cabinet according to claim 1, wherein said article support is designed and configured to support a plurality of articles in a vertical orientation, wherein said article support includes a plurality of receivers each having chamfered upper edges and depending pivot stops designed and configured to limit pivoting of the article supported in that one of said plurality of receivers.

6. A sanitization cabinet according to claim 1, wherein said article support has at least one contact region for containing a corresponding article and said article support is designed and configured to internally reflect portions of the UVL-C from said UVL-C source toward said at least one contact region.

7. A sanitization cabinet according to claim 1, wherein said article support has an article-contacting surface and comprises at least one magnet spaced from said article-engaging surface, said at least one magnet provided for holding the at least one article in a suspended state within said sanitization space.

8. A sanitization cabinet according to claim 7, wherein said article support has an article-contacting surface and comprises an elongated bar of UVL-C transparent material having exterior surfaces located so as to guide portions of the UVL-C from said UVL-C source toward said article-contacting surface.

9. An article support for a sanitizing cabinet that uses ultraviolet light type C (UVL-C) from at least one UVL-C source to sanitize at least one article, the article support comprising:
   at least one support region designed and configured to supportingly contact the at least one article at a corresponding contact zone, wherein said support region is made of a UVL-C-transparent material that allows UVL-C from the UVL-C source to illuminate the contact zone;
   wherein:
      the article support is designed and configured to be supportingly installed within the sanitizing cabinet; and
      the article support is a kitchen utensil support designed and configured to suspend one or more kitchen utensils within the sanitization cabinet.

10. An article support according to claim 9, wherein said UVL-C transparent material comprises polyethylene terephthalate glycol.

11. An article support according to claim 9, wherein the article support has at least one contact region for containing a corresponding article and the article support is designed and configured to internally reflect portions of the UVL-C from the at least one UVL-C source toward said at least one contact region.

12. An article support according to claim 9, wherein the article support has an article-contacting surface and comprises at least one magnet spaced from said article-engaging surface, said at least one magnet provided for holding the at least one article in a suspended state within said sanitization space.

13. An article support according to claim 12, wherein the article support has an article-contacting surface and comprises an elongated bar of UVL-C transparent material having exterior surfaces located so as to guide portions of the UVL-C from the at least one UVL-C source toward said article-contacting surface.

14. A cabinet comprising an article support according to claim 9.

15. A method of manufacturing an article support for an ultraviolet light type C (UVL-C) based sanitization cabinet, the method comprising:
   determining an article to be supported by the article support when the article support is installed in the sanitization cabinet and the article is placed in the sanitization cabinet for sanitizing with the UVL-C during a sanitization operation;
   locating on the article support an article support region wherein the article will be supported by the article support and will have a contact region in contact with the article support region when the article support is supporting the article within the sanitization cabinet during the sanitization operation; and
   manufacturing the article support to provide a UVL-C transparent material at the article support region so that UVL-C can reach the contact region of the article when the article support region is supporting the article within the sanitization cabinet during the sanitization operation.

16. A method according to claim 15, further comprising:
   determining at least one location where shadowing will occur on the article when the article support region is supporting the article during the sanitization operation; and
   providing the UVL-C transparent material at one or more regions of the article support selected to inhibit the shadowing.

17. A method according to claim 15, further comprising configuring portions of the article support made of the UVL-C transparent material to direct UVL-C to the contact region of the article when the article support is supporting the article during the sanitization operation.

18. An article support for a sanitizing cabinet that uses ultraviolet light type C (UVL-C) from at least one UVL-C source to sanitize at least one article, the article support comprising:
   at least one support region designed and configured to supportingly contact the at least one article at a corresponding contact zone, wherein said support region is made of a UVL-C-transparent material that allows UVL-C from the UVL-C source to illuminate the contact zone;
   wherein,
      the article support is designed and configured to be supportingly installed within the sanitizing cabinet; and
      the article support is designed and configured to support a plurality of articles in a vertical orientation, wherein said article support includes a plurality of receivers each having chamfered upper edges and depending pivot stops designed and configured to limit pivoting of the article supported in that one of said plurality of receivers.

19. A cabinet comprising an article support according to claim 18.

* * * * *